United States Patent [19]

Hesse

[11] Patent Number: Plant 6,836

[45] Date of Patent: Jun. 6, 1989

[54] CHRYSANTHEMUM PLANT NAMED SAMBA

[75] Inventor: Peter S. Hesse, Bradenton, Fla.

[73] Assignee: Ball Seed Company, Chicago, Ill.

[21] Appl. No.: 150,064

[22] Filed: Jan. 29, 1988

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Samba having anemone flower form, white ray florets and bright yellow funnelshaped disc florets, very compact and freely branching growth habits, eight week response, and a very floriferous habit.

1 Drawing Sheet

1

The present invention comprises a new and distinct cultivar of *Dendranthema grandiflora,* commonly referred to as Chrysanthemum and hereinafter referred to by the cultivar name Samba.

Samba is a product of a planned breeding program which had the objective of creating new chrysanthemum cultivars having anemone flower form; compact, freely branching habit; early flower response; white ray floret color, excellent low light, cool weather performance, and being suitable for year around pot mum programs. Such traits in combination were not present or needed improvement in previously available commercial cultivars.

Samba was originated from a hybridization made by applicant in a controlled breeding program in Parrish, Fla. in 1984. The female parent was Illini Windmill. The male parent of Samba was Frosty, disclosed in U.S. Plant Pat. No. 5,491. Samba was discovered and selected as one flowering plant within the progeny of the stated parentage by applicant on Dec. 30, 1984 in a controlled environment in Parrish, Fla.

The first act of asexual reproduction of Samba was accomplished when vegetative cuttings were taken from the initial selection in February, 1985 in a controlled environment in Parrish, Fla. by a technician working under formulations established and supervised by Peter S. Hesse. Horticultural examination of selected units initiated in November, 1985 has demonstrated that the combination of characteristics as herein disclosed for Samba are firmly fixed and are retained through successive generations of asexual reproduction.

Samba has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Samba, which in combination distinguish this chrysanthemum as a new and distinct cultivar:

1. Anemone flower form, white ray florets and bright yellow disc florets.
2. Diameter across capitulum of 5–6.5 cm.
3. Diameter of disc of 2.3–3.2 cm.

2

4. Ray florets 15–28 mm in length and 6–10 mm in width.
5. Disc florets funnelshaped and 6–13 mm in length.
6. Very compact growth habit.
7. Freely branching.
8. Medium green foliage.
9. Eight (8) week flower response.
10. Very floriferous habit.

Of the many commercial cultivars known to the present inventor, the most similar in comparison to Samba is the paternal parent Frosty. In comparison to Frosty, Samba has a one week earlier flower response, higher flower count, and performs better under winter conditions. The flower color and form of Samba are similar to those same characteristics of Frosty.

The accompanying photographic drawing shows typical inflorescence and foliage characteristics of Samba, with colors being as nearly true as possible with illustrations of this type. The photograph is in black and white, with the discs of several flowers being colored to accurately depict true color. The white ray florets are shown in their actual color.

In the following description, color references are made to The Royal Horticultural Society Colour Chart. The color values were determined between 11:30 and 11:45 a.m. on Jan. 5, 1988 under fluorescent light at Parrish, Fla.

Classification:

*Botanical.*—*Dendranthema grandiflora,* cv. Samba.

*Commercial.*—Anemone pot mum.

INFLORESCENCE

A. Capitulum:

*Form.*—Flat.

*Type.*—Anemone.

*Diameter across face.*—5–6.5 cm.

B. Corolla of ray florets:

*Color (general tonality from a distance of three meters).*—White.

*Color (upper surface).*—155D.

*Color (lower surface).*—155D.

C. Corolla of disc florets:

*Color (mature).*—6A-B.

*Color (immature).*—Yellow-green.

D. Reproductive organs:

*Androecium.*—Present in disc florets only.

*Gynoecium.*—Present in both disc and ray florets.

PLANT

A. General appearance:

*Height.*—26 cm from the top of soil; height may vary depending upon growing conditions and cultural practices.

B. Foliage:

*Color* (*upper surface*).—137A.

*Color* (*lower surface*).—137D.

*Shape.*—Ovate, lobed with serrate margins.

I claim:

1. A new and distinct cultivar of Chrysanthemum plant named Samba, as illustrated and described, and parts thereof.

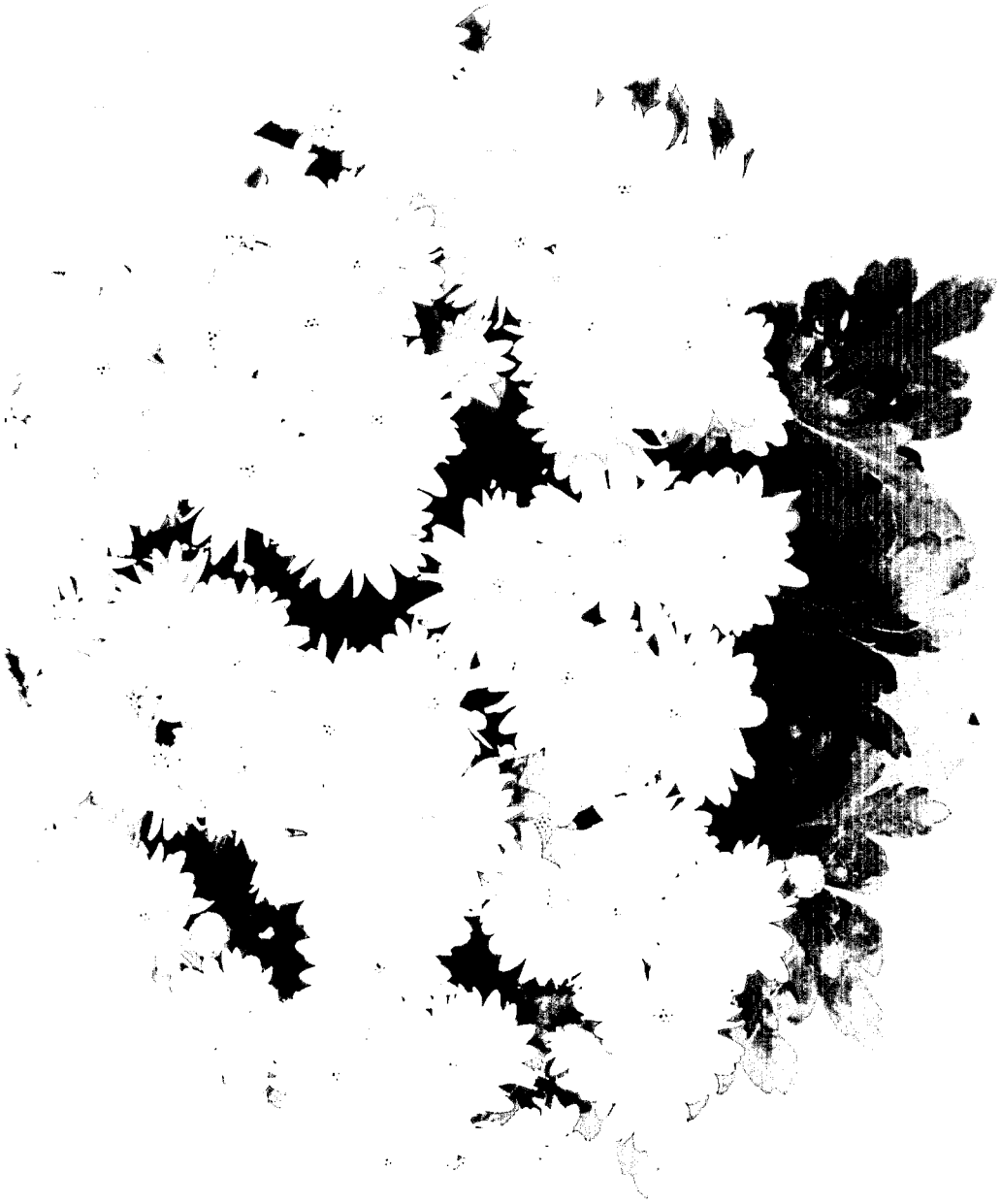

* * * * *